United States Patent [19]
Aliahmad et al.

[11] Patent Number: 5,254,091
[45] Date of Patent: Oct. 19, 1993

[54] LOW PROFILE BALLOON CATHETER AND METHOD FOR MAKING SAME

[75] Inventors: Wassim R. Aliahmad, Inglewood; Said S. Hilal, Laguna Niguel; Nabil Hilal, Mission Viejo, all of Calif.

[73] Assignee: Applied Medical Resources Corporation, Laguna Hills, Calif.

[21] Appl. No.: 639,672

[22] Filed: Jan. 8, 1991

[51] Int. Cl.⁵ ............................................. A61M 29/02
[52] U.S. Cl. ...................................... 604/96; 606/194
[58] Field of Search ..................... 606/191, 195, 194; 604/96–105

[56] References Cited

U.S. PATENT DOCUMENTS

| | | |
|---|---|---|
| 856,093 | 6/1907 | Ong . |
| 4,018,231 | 4/1977 | Wallace . |
| 4,141,364 | 2/1979 | Schultze . |
| 4,292,974 | 10/1981 | Fogarty . |
| 4,338,942 | 7/1982 | Fogarty . |
| 4,490,421 | 12/1984 | Levy . |
| 4,650,466 | 3/1987 | Luther . |
| 4,661,092 | 7/1987 | Cho . |
| 4,762,130 | 8/1988 | Fogarty . |
| 4,820,349 | 4/1989 | Saab . |
| 4,838,268 | 6/1989 | Keith et al. .......................... 606/194 |
| 4,952,357 | 8/1990 | Euteneuer . |
| 4,963,313 | 10/1990 | Noddin . |
| 5,035,694 | 7/1991 | Kasprzyk et al. ..................... 604/96 |

*Primary Examiner*—C. Fred Rosenbaum
*Assistant Examiner*—William Lewis
*Attorney, Agent, or Firm*—Richard L. Myers

[57] ABSTRACT

A non-distensible balloon is adapted to be disposed circumferentially on a tube having an elongate axis and to be compressed against the tube to achieve a low profile. The balloon includes an end wall, a central wall, and a transition wall defined by a height transition region having a first axial length and defined by a thickness transition region having a second axial length less than the first axial length. An associated method includes the step of reducing the average volume of material per unit axial length in the transition wall of the balloon relative to the average volume of material per unit axial length in either the end wall or central wall of the balloon.

5 Claims, 8 Drawing Sheets

LOW PROFILE BALLOON CATHETER AND METHOD FOR MAKING SAME

BACKGROUND OF THE INVENTION

1. Field of the Invention

The present invention relates generally to surgical devices, and more specifically to nondistensible balloon catheters.

2. Description of Prior Art

Balloon catheters are used to dilate or occlude various body conduits, cavities and openings such as blood vessels and the urethra. This is normally accomplished with a catheter formed from an elongate cannula and an inflatable balloon disposed circumferentially of the cannula near the distal end of the catheter.

In accordance with a typical procedure, the catheter is provided with the balloon in a deflated or otherwise low profile state. With this configuration, the catheter is introduced into the body conduit and positioned with the balloon in the low profile state at the point of desired dilatation. At this point the balloon is inflated or otherwise expanded to a high profile state thereby radially stretching the walls of the conduit.

This procedure is particularly applicable in the case of blood vessels which are occluded by plaque. In such a procedure, the balloon in its low profile state is positioned in proximity to the plaque. At this point the balloon is inflated to press the plaque radially against the walls of the blood vessel and thereby dilate or open the vessel to blood flow.

The procedure is also applicable for dilating large body conduits such as the gastrointestinal tract or the prostatic urethra. In the latter case, restrictions are common to men of older age where the prostate, which encircles the urethra, tends to grow inwardly thereby restricting the urethra passage. With the balloon in its low profile state, the catheter can be inserted into the urethra until the balloon is positioned in proximity to the restriction. At this point the balloon can be inflated to dilate the urethra and thereby increase the flow capacity of this conduit.

These dilatation catheters are typically characterized by nondistensible balloons which are formed from materials such as polyethylene that are relatively inflexible and therefore do not expand or distend significantly beyond a known dimension. This characteristic of nondistensibility is of particular advantage in order to insure that the vessel or conduit is not injured by overextension. Unfortunately, the relatively inflexible materials which produce the nondistensible characteristics, tend to inhibit the ability of the balloon to be rolled, compressed, collapsed, deflated or otherwise formed into a low profile state. Such a state is of particular interest in order that the catheter can be easily inserted into the vessel or conduit.

Nondistensible balloons are typically formed circumferentially and co-axially on the cannula. The balloons are characterized by two cylindrical end regions which are attached to the cannula, a cylindrical central region which is spaced from the cannula when the balloon is inflated, and a pair of conical transition regions each extending from an associated end region outwardly to the central region.

With this configuration, the nondistensible balloons of the past have been blow molded from materials which are commonly provided in the configuration of a tube having a substantially constant wall thickness. In the blow molding process, the walls of the tube are expanded against the inner surface of a mold which is provided with a shape desired for the balloon. Ends of the balloon remain at the initial diameter and thickness of the tube, while the central region of the balloon expands to the maximum diameter and minimum wall thickness of the balloon. It is these walls in the central region, which may have a thickness reduced by a factor as much as 100, that dictate the strength of the balloon. Between the central region and each of the end regions of the balloon, one of the transition zones is characterized by a wall thickness which varies from the original thickness of the wall of the tube to the reduced thickness of the wall of the central region.

When these nondistensible balloon catheters are initially inserted, it is of particular importance that the balloon be rolled on the catheter tube to the smallest diameter in order to provide the catheter with the lowest profile possible. The rolling of the balloon has not been a problem in the end regions. Even though end walls contain the thickest wall section, they are fixed in close proximity to the cannula and therefore maintain a low profile even when the balloon is inflated. Similarly, rolling the balloon on the cannula has not been a problem in the central region. Even though the walls in this region are disposed at the highest radial distance from the cannula, the very thin walls in this region are adaptable to being rolled into close compliance with the cannula. However, in the transition regions of the balloon, both the thickness of the wall and the radial displacement of the wall tend to create a problem. Although the transition wall is thinner than that in the end region, it is disposed at a greater radial distance than the end wall. And although this radial distance is less than that of the central region, the wall thickness is greater and therefore more rigid than the central region.

When a nondistensible balloon of the past has been rolled onto a cannula, it has resulted in enlarged sections at each transition region, giving the rolled balloon the appearance of a dog bone. These enlarged transition sections typically have diameters as much as 50% greater than those associated with either the central section or the end section of the rolled balloon. Furthermore they tend to form sharp corners which can severely damage the body conduit during both insertion and withdrawal of the catheter.

With these deficiencies of the prior art, it is an object of the present invention to provide a balloon catheter wherein the balloon can be rolled or otherwise compressed onto the catheter tube to a diameter which is substantially constant along the entire length of the rolled balloon.

SUMMARY OF THE INVENTION

In accordance with the present invention, a balloon catheter is provided wherein the balloon can be rolled on the catheter tube to a profile which is substantially constant in diameter along the length of the balloon. Furthermore, there are no sharp points associated with this low profile. As a result, the greatest diameter of the catheter with the balloon in its low profile state, is reduced by as much as 50% with substantially no sharp edges to damage the body conduit.

In one aspect of the invention, a nondistensible balloon is adapted to be rolled on a cannula having an elongate axis, in order to achieve a low profile. The balloon comprises an end wall disposed in an end region of the balloon and having a fixed circumferential relationship with the cannula. A central wall disposed in a central region of the balloon is displaced from the cannula when the balloon is inflated. A transition wall disposed between the end wall and the central wall includes a height transition region where the transition wall extends from the height of the end wall to the height of the central wall, and a thickness transition region where the transition wall extends from the thickness of the end wall to the thickness of the central wall. The axial length of the thickness transition zone is less than the axial length of the height transition zone.

In another aspect of the invention, a method for making a nondistensible balloon characterized by an end wall, central wall and transition wall, includes the step of providing a blow mold having an end wall surface, a central wall surface and a transition wall surface equivalent to the external shape desired for the respective end wall, central wall and transition wall when the balloon is inflated. The method further comprises the steps of inserting a tube of material into the mold and blow molding the material of the tube against the surface of the mold. Finally, the process calls for reducing the quantity of material per unit length in the transition wall to an amount less than the average volume of material per unit length in either the end wall or the central wall of the balloon.

In other aspects of the invention, the traditional blow molding method is altered by providing the tube of material with a reduced wall thickness in those areas which correspond to the transition regions of the balloon. This automatically reduces the quantity of material and hence the thickness of the transition walls.

In another method, a balloon formed in accordance with the prior art is inserted into a funnel or mold which is configured to receive at least the transition wall of the balloon. This second mold is heated to increase the flexibility of the balloon in the transition region, and the balloon is stretched axially to thin the heated wall.

In still a further method, the blow mold is formed with recesses in the transition surface. In such a mold, the balloon is formed with projections in the transition region, which increase the surface area and therefore decrease the thickness of the transition walls.

These and other features and advantages of the invention will be more apparent with a description of preferred embodiments and reference to the associated drawings.

DESCRIPTION OF PREFERRED EMBODIMENTS

Figure 1:
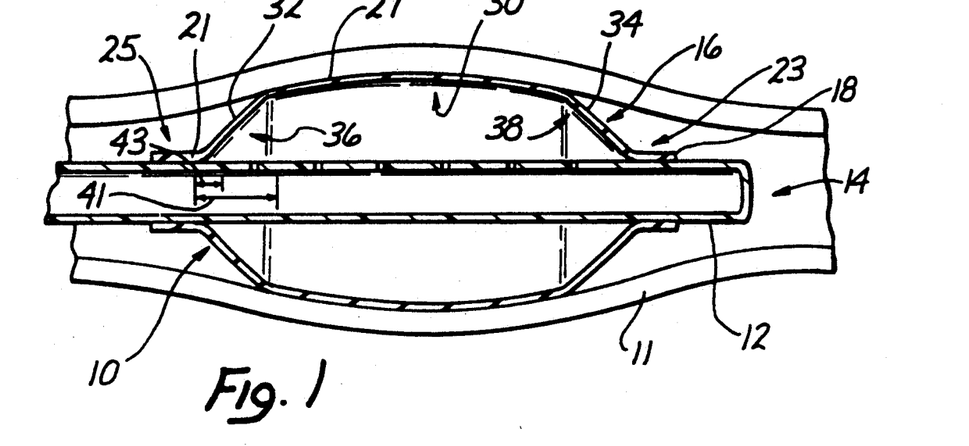
FIG. 1 is an axial cross-section view of one embodiment of a balloon catheter of the present invention, showing the catheter operatively disposed in a body conduit.

A dilatation catheter is illustrated generally in FIG. 1 and designated by the reference numeral 10. The catheter 10 is operatively disposed in a body conduit defined by walls 11, and includes an elongate cannula 12 having a distal end 14 and a proximal end (not shown).

The catheter 10 also includes a balloon 16 having a distal end wall 18 and a proximal end wall 21 disposed in respective end regions 23 and 25 of the balloon 16. A central wall 27 is disposed between the end walls 18 and 21 in a central region 30 of the balloon 16.

In this particular embodiment the end walls 18 and 21 are relatively thick and relatively small in diameter This is in comparison to the central wall 27 of the balloon 16 which is relatively thin and relatively large in diameter.

A pair of transition walls 32 and 34, each having a generally conical configuration, are of particular interest to the present invention. The transition wall 32 is disposed in a proximal transition region 36 between the end region 25 and the central region 30. The transition wall 34 is disposed in a distal transition region 38 between the end region 23 and the central region 30 of the balloon.

Two separate transitions occur to the walls 32, 34 in each of the transition regions 36, 38. First, the walls 32, 34 are each characterized by a transition in height from the height of the respective end walls 18, 21 to the height of the central wall 27. This transition region will be referred to as the height transition region 41. Second, in the transition regions 36, 38 the walls 32, 34 respectively, undergo a transition from their greatest thickness in proximity to the end region 25, 23 respectively, to their least thickness in proximity to the central region 30. This transition region is referred to as the thickness transition region 43. It is the relative axial length of the two regions of transition, the height transition region 41 and the thickness transition 43, which are of particular interest in this case.

In accordance with the present invention, the thickness transition region 43 has a shorter axial dimension than does the height transition region 41. This occurs because the thickness of the end wall 21 thins to a dimension generally equivalent to the thickness of the central wall 27 over a relatively short distance along the transition wall 32. It is particularly desirable that this thickness transition region 43 be positioned in close proximity to the end wall 21 so that any substantial wall thickness associated with the region 43 is closely spaced to the outer surface of the cannula 12.

Figure 2:
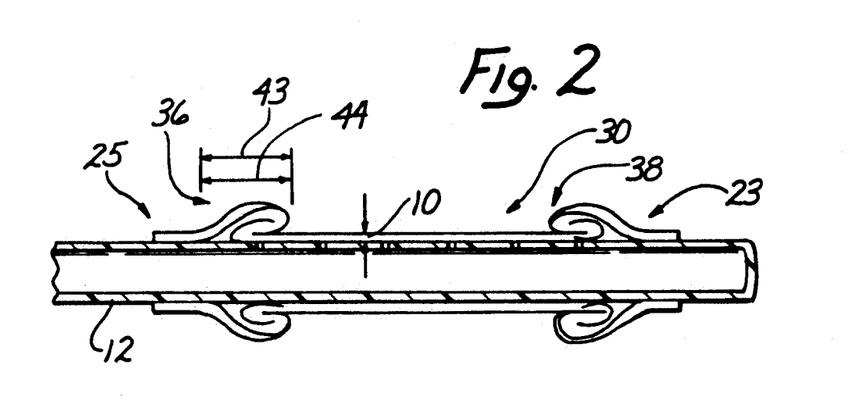
FIG. 2 is an axial cross-section view of a balloon associated with the prior art rolled onto a cannula and illustrating the dog bone profile associated with the prior art.

As will be discussed in greater detail below, the balloons of the prior art have a thickness transition region 43 which is generally equivalent in axial length to the height transition region 41. In other words, the thickness of the transition wall 32 gradually decreases over the entire axial distance between the end region 25 and the central region 30. While this does not adversely affect the balloon in its inflated, high profile state, it has a dramatic affect on the rolled, low profile state of the balloon as illustrated in FIG. 2. With the relative thickness of the transition wall spaced even a short radial distance from the cannula 12, the balloon 10 in its rolled configuration tends to have an undesirable dog bone shape. Thus in the low profile state, in the low profile state, enlargements occur at both of the transition regions 36 and 38 with the balloon of the prior art. It is in these regions that the respective walls 32 and 34 are too thick and too far displaced from the cannula 12 to adequately comply to the cannula in the rolled state.

Figure 3:
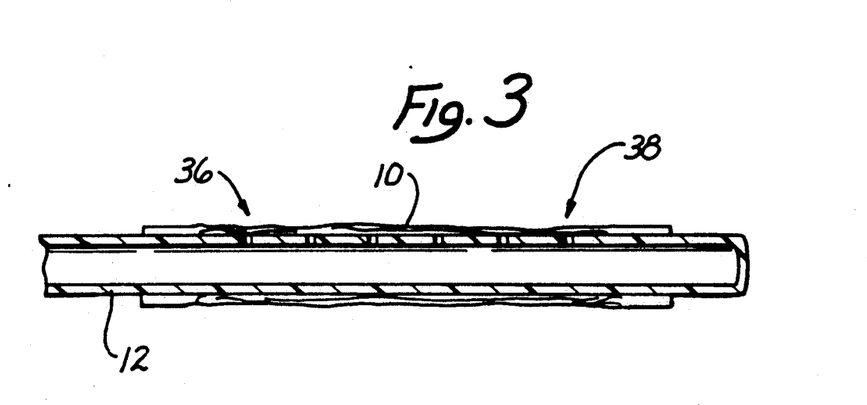
FIG. 3 is an axial cross-section view illustrating the low profile, rolled characteristics associated with the balloon of FIG. 1.

By thinning the walls 32 and 34 of the transition regions 36, 38 respectively, the walls of the balloon 16 are either thick in proximity to the cannula 12 or thin at any substantial radial distance from the cannula 12. It is in this manner that the balloon of FIG. 1 in the rolled configuration achieves a low profile state as illustrated in FIG. 3.

An understanding of the wall thickness associated with the transition zones 36, 38 and its effect on the rolled configuration of the balloon 10 will be better understood with reference to a typical blow molding process used to manufacture the balloon of the prior art. FIG. 4 and FIGS. 4a-4d illustrate steps in a blow molding process of the prior art; however, some of these steps also apply to the methods associated with the present invention.

Figures 4, 4A, 4B:
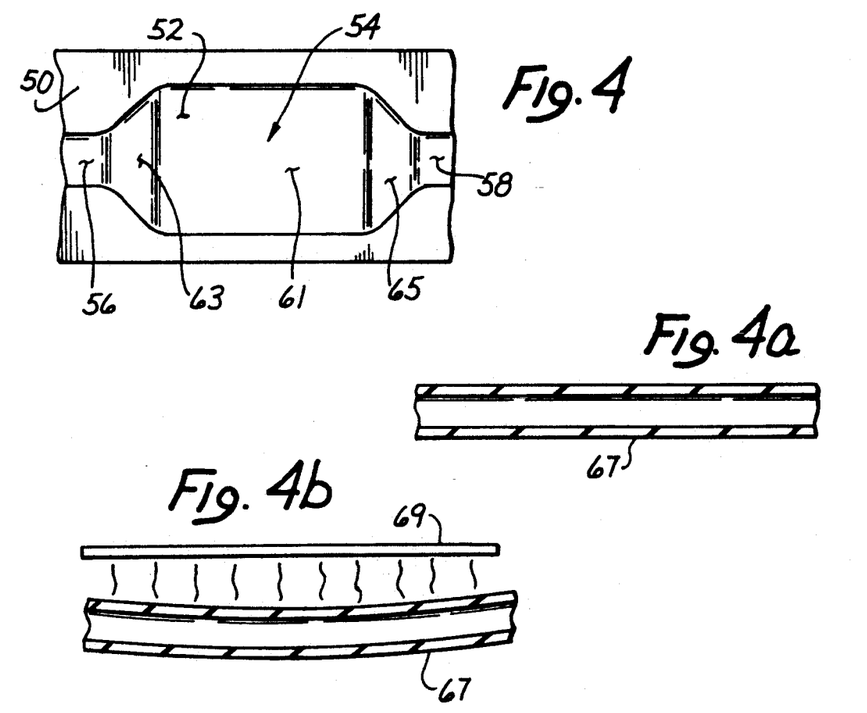
FIG. 4 illustrates a top plan view of a blow mold used in the prior art method for making the balloon illustrated in FIG. 2.
FIG. 4a is an axial cross-section view of blow mold tubing used in the prior art method.
FIG. 4b is an axial cross-section view of the tubing of FIG. 4a being heated in the prior art process.
Figure 4C:
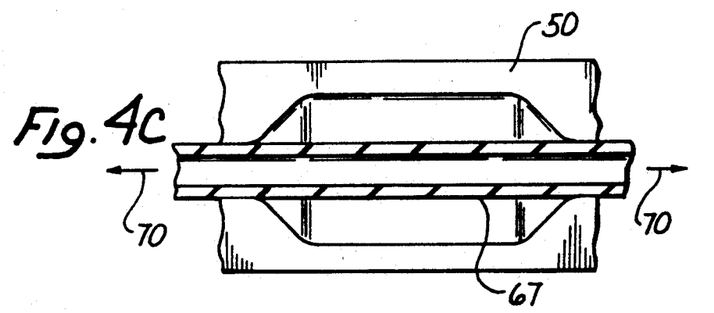
FIG. 4c is an axial cross-section view of the tubing of FIG. 4 coaxially disposed in the mold of FIG. 4.

In the plan view of FIG. 4, a blow mold 50 is illustrated with an inner mold surface 52 which defines a cavity 54 having the shape desired for the external surface of the balloon 16. Thus the surface 52 includes end surfaces 56, 58 which correspond to the end regions 23, 25 respectively, a central surface 61 which corresponds to the central region 30, and transition surfaces 63, 65 which correspond to the transition regions 36, 38 respectively.

In accordance with this process of the prior art, material is provided in the form of a tube 67 which has a generally cylindrical configuration and a relatively constant wall thickness as illustrated in FIG. 4a. The tube 67 is heated, for example in a conventional oven 69, to provide the tube 67 with a generally limp, pliable configuration. In this state, the tube 67 is inserted into the mold 50 and stretched axially as shown by the arrows 70 in FIG. 4c. This axial stretching tends to align the tube 67 coaxially with the cavity 54 of the mold 50.

Figure 4D:
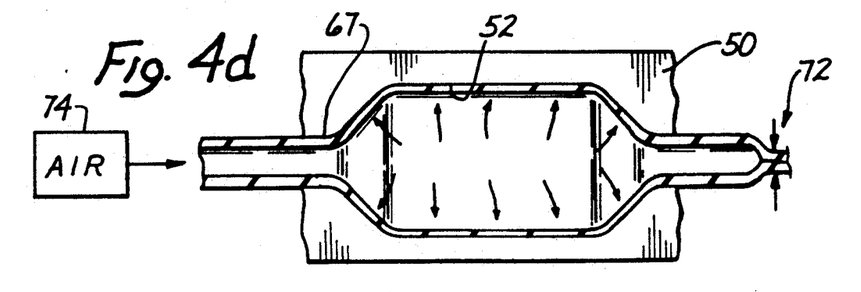
FIG. 4d illustrates the blow molding step in the process of the prior art.

At this point in the process, one end of the tube 67 is sealed by a clamp shown generally at 72 in FIG. 4d. The other end of the tube 67 is inflated by a fluid, such as air, provided by a compressor 74. This air is blown into the heated tube 67 stretching the walls of the tube 67 until they contact the surface 52 of the mold 50. Upon contact, the walls of the balloon 16 are cooled by the mold 50 and frozen in their expanded state.

It will be apparent with reference to FIG. 4d that the volume of material per unit length provide by the tube 67 will also be equivalent to the volume of material per unit length of the walls forming the balloon 16. Where the central wall 27 is greatly spaced from the axis of the balloon, this constant volume will necessarily require a relatively thin central wall 27. Where there is substantially no radial displacement of the tube 67, for example in the end region 23, 25 the thickness of the respective end walls 18, 21 will be substantially the same as the thickness as the walls of the tube 67. Along the transition walls 32, 34, the result achieved with the formation of the end walls 18, 21 gives way to the result achieved with the formation of the central wall 27. Thus the greater the radial displacement of the walls of the tube 67, the less the thickness of the resulting wall of the balloon 16.

In a further description of the invention, focus will be directed primarily to the transition region 36 illustrated in the upper left hand corner of the balloon 16 in FIG. 1. However, the comments will apply equally as well to the quadrant of the balloon 16 in the lower left hand corner of FIG. 1. Comments may also apply to transition region 38 illustrated on the right hand side of the balloon 16 of FIG. 1.

Figure 5:
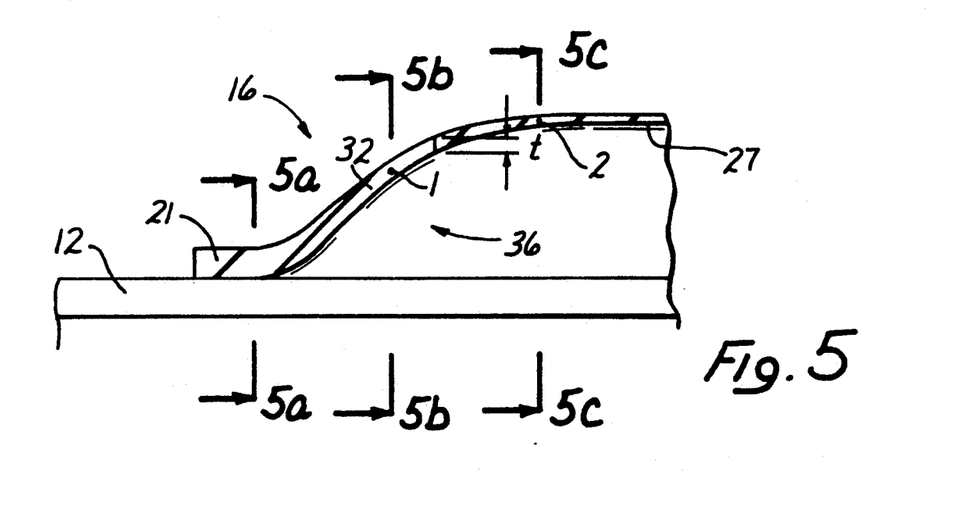
FIG. 5 is an enlarged axial cross-section view of one quadrant of the balloon of the prior art illustrated in an inflated state.

The transition region, such as the region 36, is illustrated for a balloon of the prior art in the enlarged view of FIG. 5. In this view it is apparent that the thickness transition zone 43 is substantially equivalent in axial dimension to the thickness transition zone 41. Because there is substantial thickness of the wall 32 in the transition zone 36 at substantial radial dimensions from the cannula 12, the balloon 16 in the rolled configuration has the dog bone profile illustrated in FIG. 2. The thickness of the walls 21, 32 and 27 is measured and discussed with respect to their dimension in a radial plane as illustrated by the thickness "t" in FIG. 5.

Figure 5A:
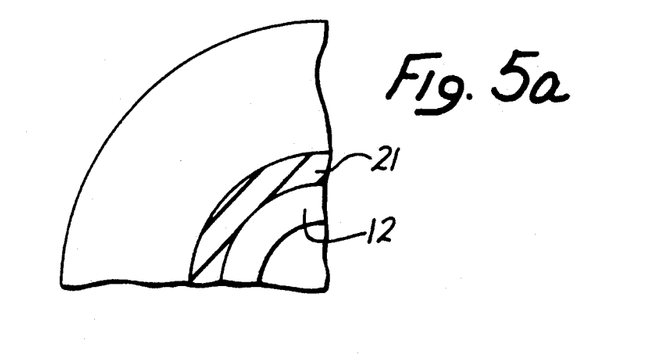
FIG. 5a is a cross-sectional view taken along lines 5a—5a of FIG. 5.
Figures 5B, 5C:
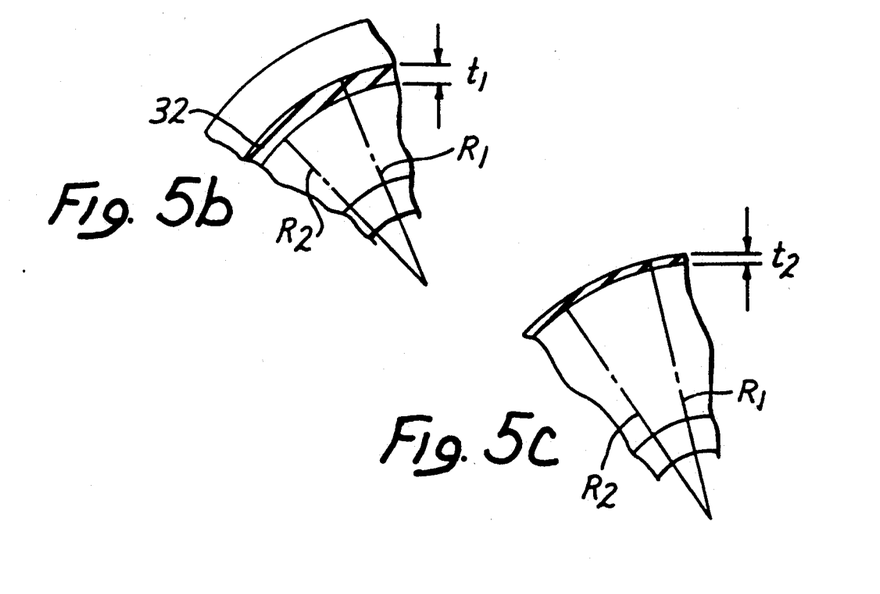
FIG. 5b is an axial cross-section view taken along lines 5b—5b of FIG. 5.
FIG. 5c is an axial cross-section view taken along lines 5c—5c of FIG. 5.

As long as the volume of material per unit axial length remains constant along the walls of the balloon 16, as is the case with the balloons of the prior art, a relationship can be established based on the thickness "t" at any two locations along the balloon walls. FIGS. 5a, 5b and 5c show radial cross-sections of the prior art balloon in FIG. 5 taken along the lines 5a, 5b and 5c respectively. Referring to FIG. 5b, the transition wall 32 has a thickness $t_1$ at a point "1" in FIG. 5. This thickness $t_1$ is equivalent to the difference between the inner radius $r_1$ and the outer radius $R_1$ of the wall 32.

Similarly in FIG. 5c, the wall of the balloon 16 has a thickness $t_2$ at a point "2" between the central region 30 and the transition region 36. This thickness $t_2$ is equivalent to the difference between the inner radius $r_2$ and the outer radius $R_2$ of the wall 32. If the volume per unit length of material in the walls 21, 32 and 27 is equivalent, as is the case with the balloons of the prior art, then the shaded areas in FIGS. 5b and 5c will be equivalent in size. It follows that the thickness of the wall at any point, such as the point 1, can be determined given the radii $r_1$ and $R_1$, the thickness at any point 2 and the associated radii $r_2$ and $R_2$ at point 2. It follows that this relationship is established by the following Formula I:

$$t_1 = t_2 \left( \frac{r_2 + R_2}{r_1 + R_1} \right)$$

This relationship has existed in the prior art and has given rise to the noncompliant, dog bone shape of the balloon 16 in its low profile configuration as illustrated in FIG. 2. In accordance with the present invention, the thickness $t_1$ will be given by the following Formula II:

$$t_1 < t_2 \left( \frac{r_2 + R_2}{r_1 + R_1} \right)$$

Figure 6:
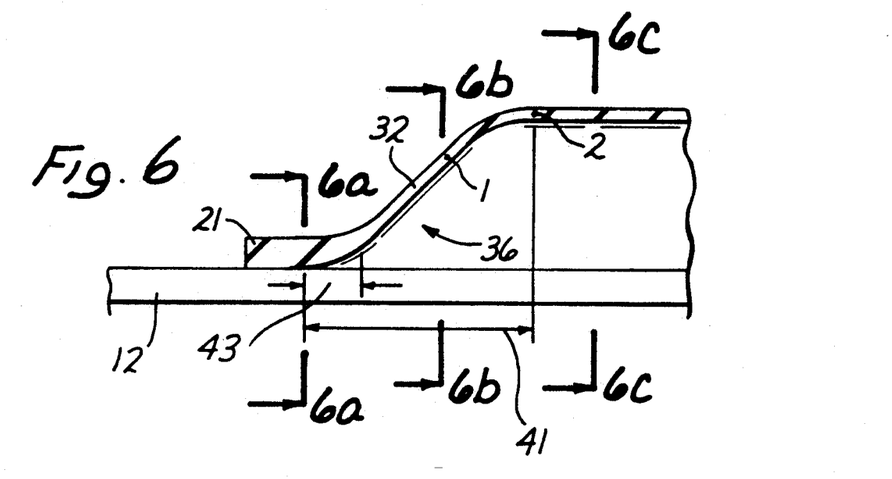
FIG. 6 is an axial cross-section view of one quadrant of the balloon of FIG. 1 illustrated in an inflated state.
Figure 6A:
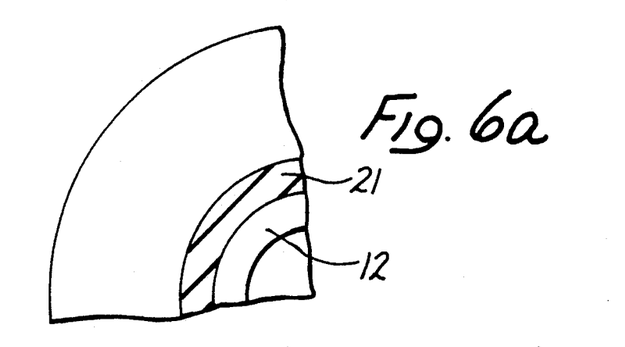
FIG. 6a is a cross-sectional view taken along lines 6a—6a of FIG. 6.
Figures 6B, 6C:
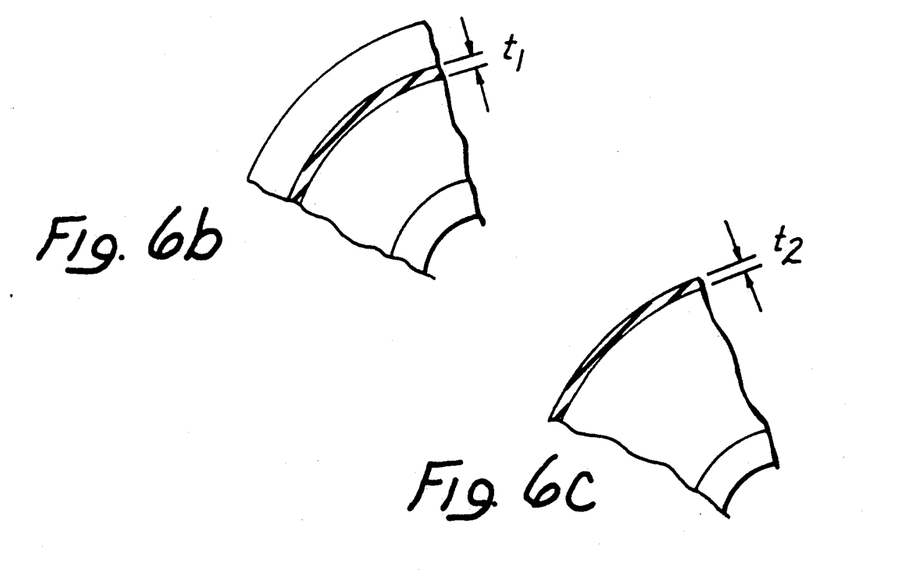
FIG. 6b is an axial cross-section view taken along lines 6b—6b of FIG. 6.
FIG. 6c is an axial cross-section view taken along lines 6c—6c of FIG. 6.

This is illustrated in the embodiment of FIG. 6 where the thickness $t_1$ at the point 1 is substantially equivalent to the thickness $t_2$ at the point 2. The conditions of Formula II will be met since the sum of $r_1+R_1$ is less than the sum of $r_2+R_2$. This can be appreciated by merely noticing that the shaded area in FIG. 6b has a smaller area than does the shaded area in FIG. 6c.

In particular embodiments of the invention, it is desirable that the axial length of the thickness transition region 43 be maintained at less than one-half the axial length of the height transition region 41. In the most preferred embodiment, the full transition in thickness from the thickness wall 21 to the thinnest wall 27 occurs within only one-fourth of the axial distance along the height transition region 41. Of course, the maximum advantage is achieved where the wall 32 is consistently thin throughout the entire height transition region 41. And in an ideal case, the end wall 21, the transition wall 32, and central wall 27 all have the same thinness. Even in this case the strength of the balloon is still determined by the thickness of the central wall 27.

Figure 7:
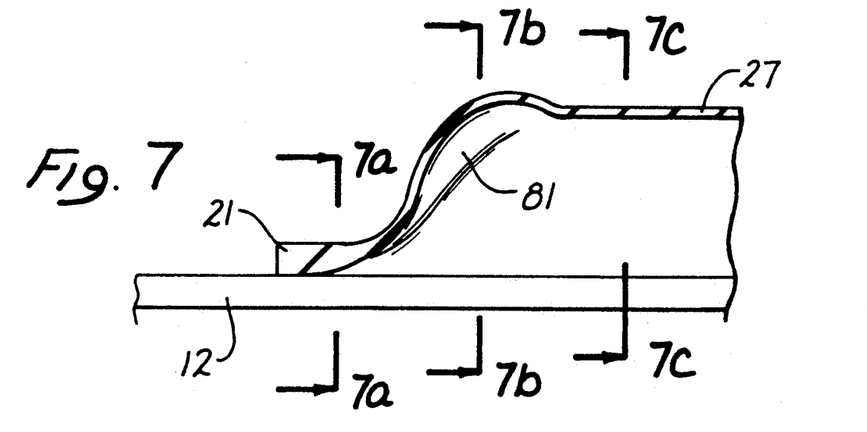
FIG. 7 is an axial cross-section view similar to FIG. 6 of a further embodiment of the balloon associated with the present invention.
Figure 7A:
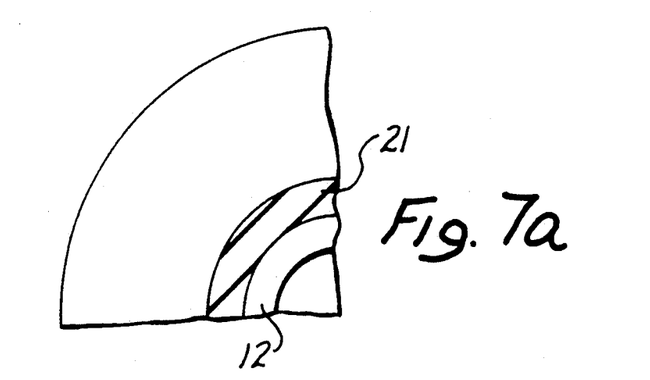
FIG. 7a is a cross-sectional view taken along lines 7a—7a of FIG. 7.
Figure 7B:
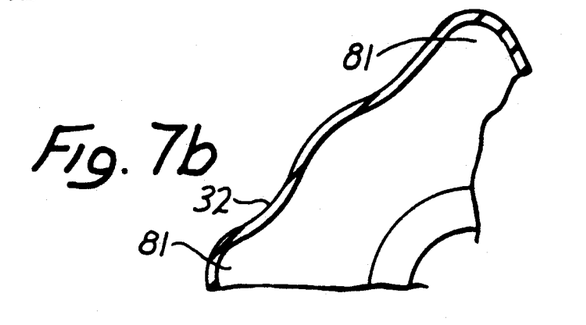
FIG. 7b is an axial cross-section view taken along lines 7b—7b of FIG. 7.
Figure 7C:
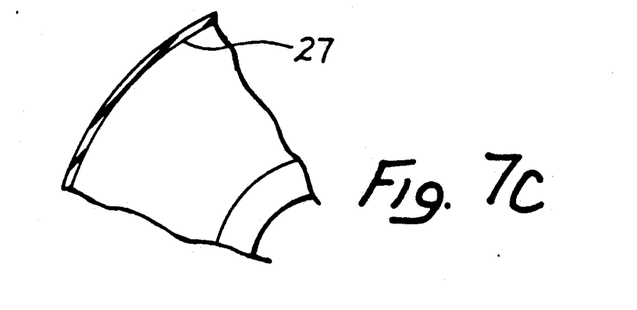
FIG. 7c is an axial cross-section view taken along lines 7c—7c of FIG. 7.

This reduced wall thickness of the transition region 36 can be provided in an embodiment where the walls 32 are provided with an increased area so that they are automatically thinned due to the scarcity of the material. In the embodiment of FIG. 7, the increased area in the transition region 36 is provided in the form of projections 81. By adding these projections 81, the area of the balloon in the region 36 is increased so that the thickness of the wall 32 is substantially equivalent to the wall 27. In such an embodiment, the thin walls in the transition region 36 are as compliant as the walls 27 in the central region 30. This facilitates rolling the balloon into a low profile state as illustrated in FIG. 3.

Figure 8:
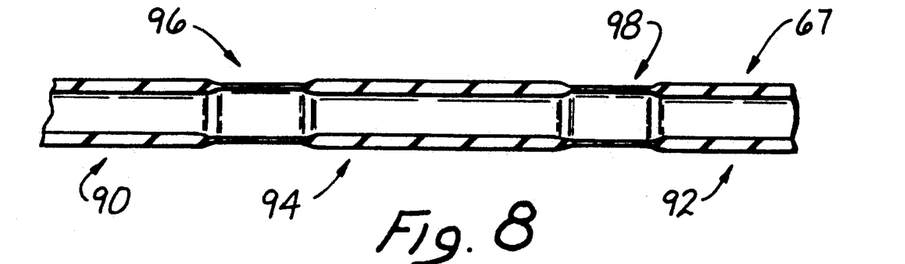
FIG. 8 is an axial cross-section view of bump tubing used in a method of the present invention.
Figure 8A:
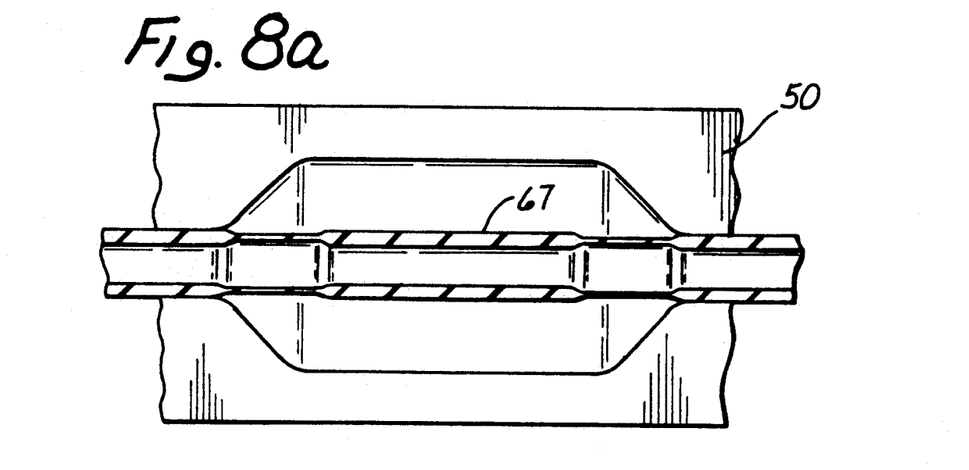
FIG. 8a is an axial cross-section view of the bump tubing of FIG. 8 inserted in a conventional blow mold associated with the present invention.
Figure 8B:
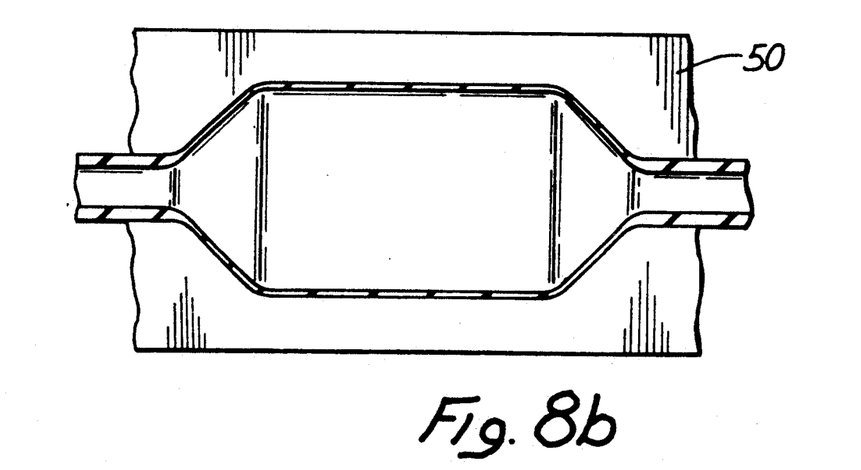
FIG. 8b is an axial cross-section view showing the molded balloon with a transition wall of substantially constant thickness.

The balloons of the present invention also can be made in accordance with a preferred method shown by the steps illustrated in FIGS. 8-8b. Thus the process of FIG. 4 can be revised in the step illustrated in FIG. 4a by providing the tube 67 in a configuration illustrated in FIG. 8. In this case, the tube 67 has walls of generally constant thickness in a pair of end zones 90 and 92 which are associated with the end regions 23 and 25 respectively of the balloon 16. The wall of the tube 67 has a greater cross sectional area in a central zone 94 which is associated with the central region 30 of the balloon 16. Between each of the zones 90, 92 and the central zone 94, a pair of transition zones 96, 98 respectively, are provided which supply the material associated with the transition regions 36 and 38 of the balloon 16.

The walls of the tube 67 in the transition zones 96, 98 have reduced cross-sectional area relative to the walls in the central zone 94. When the tube of FIG. 8 is inserted into the mold 50 as illustrated in FIG. 8a, the reduced material available in the transition zones 96, 98 automatically produces a balloon 16 with transition regions 36, 38 of reduced thickness. In this manner, the balloon of FIG. 1 can be produced in accordance with the method steps illustrated in FIGS. 8-8b.

Figures 9, 9A, 10:
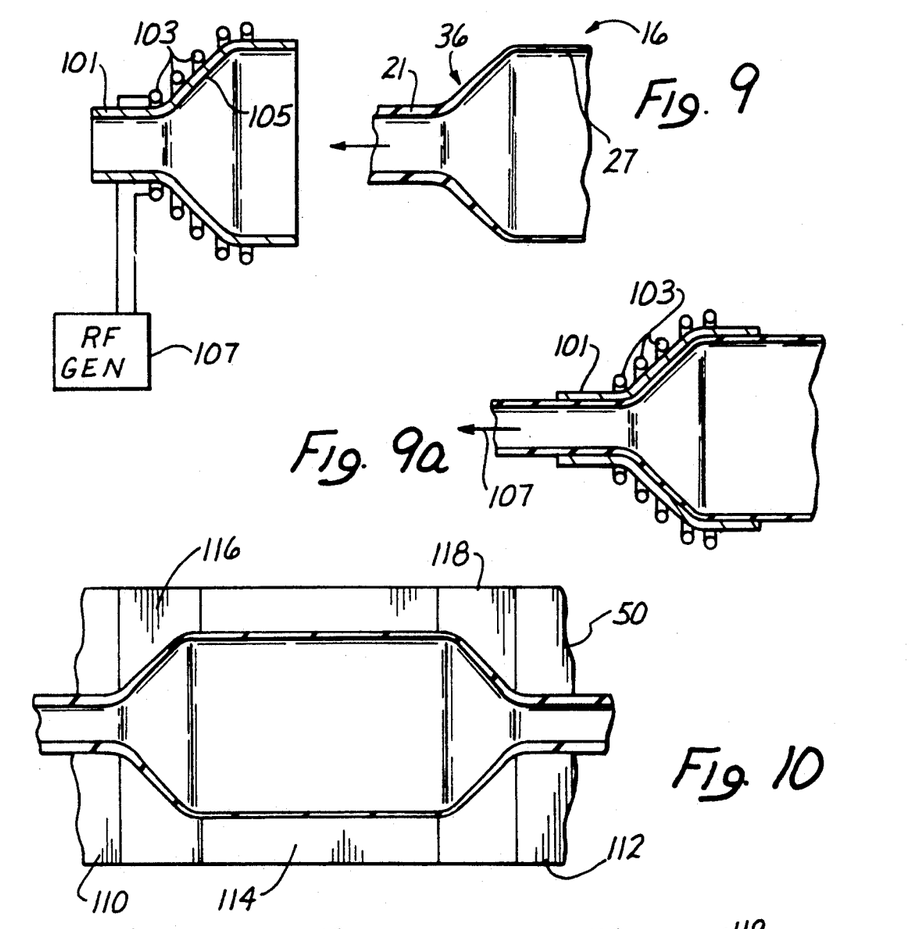
FIG. 9 is an axial cross-section view of a second mold or funnel associated with a further method of the present invention.
FIG. 9a illustrates a balloon disposed in the funnel of FIG. 9, heated, and stretched in the transition region to form a transition wall of reduced thickness.
FIG. 10 is a top plan view of a blow mold associated with a further method of the present invention.

Referring to FIGS. 9 and 9a, it will be apparent that all of the steps associated with FIGS. 4-4d which produce the prior art balloon of FIG. 5, are equally applicable to an improved process wherein a second mold is provided in the shape of a funnel 101. The funnel 101 can be formed from stainless steel or other suitable material and surrounded by induction coils 103. An inner surface 105 of the funnel 101 is provided with the shape desired for the exterior surface of the balloon 16 particularly in the transition region 36.

In this extended process the induction coils 103 can be energized by a signal from a radio frequency generator 107. This radio frequency energy is inductively coupled to the funnel 101 to heat the interior surface 105. Inserting the balloon 16 of the prior art into the funnel 101, as illustrated in FIG. 9, heats the transition zone 36. When axial tension is applied to the end wall 21 of the balloon 16, as illustrated by the arrow 109, the heated transition wall thins to the reduced thickness illustrated in FIG. 6.

Figure 10A:
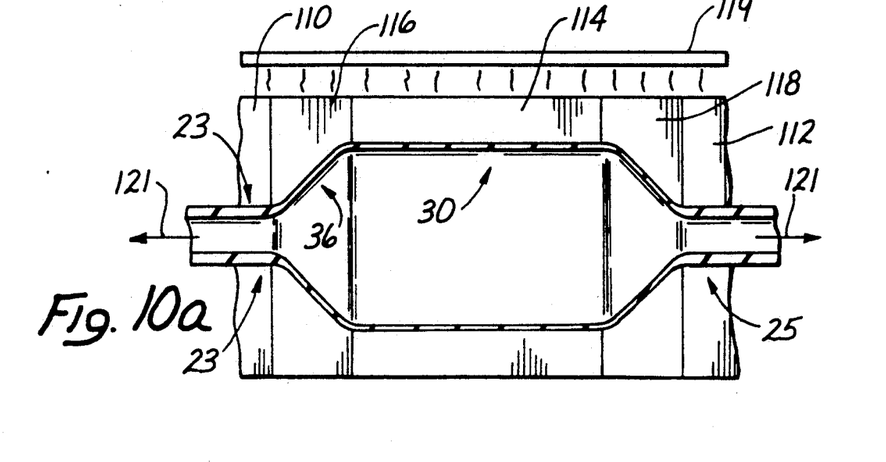
FIG. 10a is an axial cross-section view of the balloon disposed in the mold of FIG. 10, heated, and axially stretched in the transition regions to provide a transition wall of reduced thickness.
Figure 11:
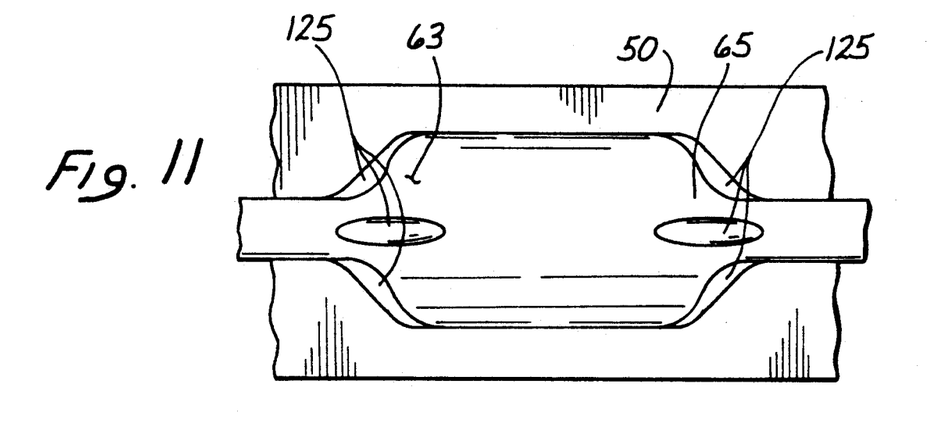
FIG. 11 is a top plan view of a mold associated with a further method of the present invention.

In a similar method illustrated in FIGS. 10 and 10a, the mold 50 is provided with a pair of end sections 110 and 112, a central section 114, and a pair of transition sections 116 and 118 In this case, the material forming the transition sections 116, 118 and the end sections 110 and 112, is preferably heat conductive, such as metallic, while the material forming the central section 114, is preferably non-heat conductive such as plastic.

With the balloon 16 disposed in the mold 50, the entire mold can be heated by a heater 119 to increase the temperature of the metallic sections 116, 118, 110 and 112. The plastic section 114, however, will not easily transmit the heat so the central region 30 of the balloon 16 remains relatively cool. By axially stretching the balloon 16 under these conditions, the heated material in the transition regions 36, 38 and the end regions 110, 112 will be thinned to provide the balloon 16 with the configuration illustrated in FIG. 8b.

In still a further method of the present invention the mold 50 illustrated in FIG. 4 can be modified by providing recesses 125 in the transition surfaces 63 and 65. Using the remainder of the steps illustrated in FIGS. 4a–4d will produce a balloon 16 having the configuration illustrated in FIG. 7. With the reduced wall thickness provided by the projections 81, the balloon 16 can be rolled to a low profile state as illustrated in FIG. 3.

As previously discussed, the strength of the balloon 16 is dictated primarily by the wall thickness in the central region 30 while the problems associated with the low profile are dictated primarily by the wall thickness in the transition zones 36, 38. The prior art has not been able to develop reduced wall thicknesses in the transition zones 36 and 38 which are sufficiently thin to avoid the dog bone effect without sacrificing strength in the central region 30.

Figure 12:
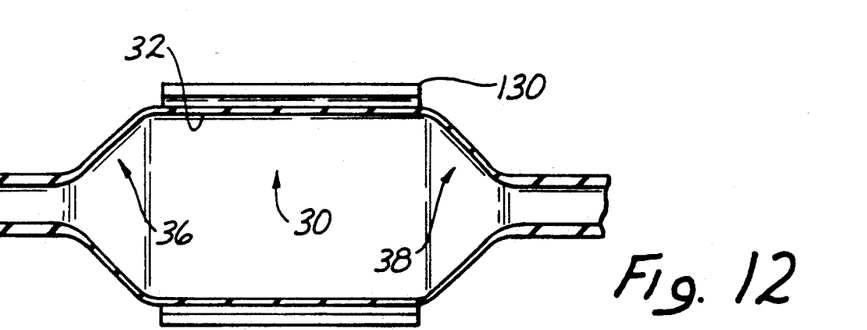
FIG. 12 is an axial cross-section view of a conventional balloon with a sleeve bonded to the central regions of the balloon.

In order to reduce wall thicknesses in the transition regions of the prior art, it has required that the wall thicknesses in the central region 30 also be reduced below the thickness required for minimum strength. However, it will now be possible in accordance with the concept of the present invention to form just such a balloon with reduced wall thicknesses in the transition regions 36 and 38, and then to reinforce the central region 30, for example with a sleeve 130 as illustrated in FIG. 12. Bonding the sleeve 130 onto the central wall 27 will increase the strength of this critical central region 30 without otherwise increasing the thickness of the walls in the transition regions 36 and 38.

Figure 13:
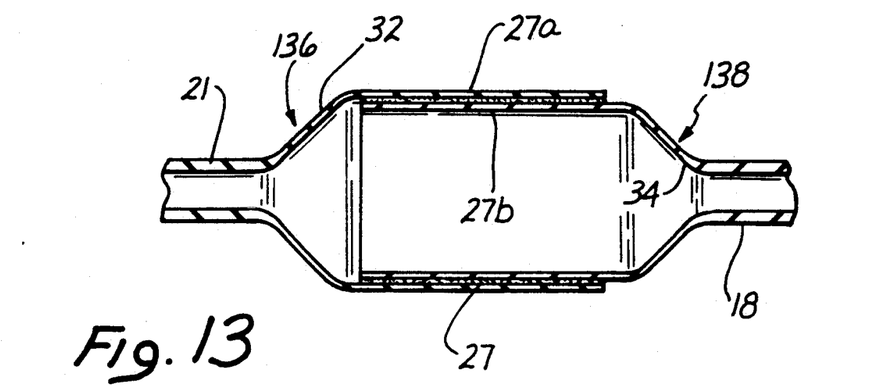
FIG. 13 is an axial cross-section view of two balloon portions wherein central regions of each balloon portion are overlapping and bonded to increase the thickness of the central wall of the balloon.

It is also within the scope of the present invention to provide two separate wall sections each formed in accordance with the method of FIG. 4. For example, in FIG. 13, a wall section 136 is illustrated to include the end wall 21, the transition wall 32 and a central wall 27a. Similarly, a second balloon section 138 includes the end wall 18, the transition wall 34 and a central wall 27b. The central wall 27b can be inserted into the central wall 27a and bonded in this position. The resulting wall in the central region 30 will have a double, reinforced thickness without increasing the thickness of the transition walls 32 or 34.

Although the invention has been described with reference to preferred embodiments and methods, it will be apparent that the balloon and catheter associated with the present invention can be otherwise embodied and manufactured. For example, in all of the foregoing examples requiring a blow mold, the mold can be entirely eliminated in which case the balloon is free formed. In the absence of a mold, control over the ultimate shape of the balloon is somewhat restricted. Nevertheless, the concepts disclosed herein for reducing the wall thicknesses particularly in the transition region of the balloon are equally applicable. Due to these variations in the concept, one should not refer merely to the drawings or the particular embodiments discussed. Rather, the scope of the invention should be ascertained only with reference to the following claims.

We claim:

1. A non-distensible balloon adapted to be disposed circumferentially on a tube having an elongate axis, and adapted to be rolled on the tube to achieve a low profile, the balloon comprising:
   an end wall disposed in an end region of the balloon and in a fixed circumferential relationship with the tube;
   a central wall disposed in a central region of the balloon and in a displaced relationship with the tube when the balloon is inflated;
   a transition wall extending from the end wall to the central wall of the balloon, the transition wall defining;
   a height transition region wherein the transition wall extends from a first radius at the end wall to a second radius at the central wall, the height transition region having a first axial length, and
   a thickness transition region wherein the transition wall varies from a maximum thickness to a minimum thickness, the thickness transition region having a second axial length less than the first axial length;
   first portions of the balloon disposed in the transition wall and having a thickness $t_1$, an inside radius $r_1$, and an outside radius $R_1$; and
   second portions of the balloon disposed in one of the end wall, central wall and the transition wall, and having a thickness $t_2$, an inside radius $r_2$ and an outside radius $R_2$;
wherein
   the thickness $t_1$ of the first portions of the balloon is characterized by the following formula:

$$t_1 < t_2 \left( \frac{r_1 + R_1}{r_2 + R_2} \right).$$

2. The non-distensible balloon recited in claim 1 wherein the second axial length of the thickness transition region is less than one half the first axial length of the height transition region.

3. The non-distensible balloon recited in claim 1 wherein the thickness of the transition wall is constant between two different locations along the height transitions region.

4. The non-distensible balloon recited in claim 1 wherein the entire thicknesstransition transition region is disposed within an axial distance from the end zone equal to one half the axial length of the height transition region.

5. The non-distensible balloon recited in claim 1 wherein the thickness $t_1$ of the first portions of the balloon is characterized by the following formula:

$$t_1 < \frac{1}{2} t_2 \left( \frac{r_1 + R_1}{r_2 + R_2} \right)$$

* * * * *

UNITED STATES PATENT AND TRADEMARK OFFICE
CERTIFICATE OF CORRECTION

PATENT NO. : 5,254,091
DATED : October 19, 1993
INVENTOR(S) : Wassim R. Aliahmad, Said S. Hilal, Nabil Hilal It is certified that error appears in the above—identified patent and that said Letters Patent is hereby corrected as shown below:

Col. 10, line 53, after "entire" delete "thicknesstransition transition" and add -- thickness transition --.

Signed and Sealed this

Twenty-third Day of August, 1994

Attest:

BRUCE LEHMAN

Attesting Officer

Commissioner of Patents and Trademarks